United States Patent [19]

McCormick et al.

[11] Patent Number: 5,045,071
[45] Date of Patent: Sep. 3, 1991

[54] DOUBLE WALL CATHETER WITH INTERNAL PRINTING AND EMBEDDED MARKER

[75] Inventors: William McCormick, Carlisle; Miles C. O'Donnell, Andover, both of Mass.

[73] Assignee: MBO Laboratories, Inc., North Chelmsford, Mass.

[21] Appl. No.: 299,237

[22] Filed: Jan. 19, 1989

Related U.S. Application Data

[63] Continuation of Ser. No. 196,047, May 19, 1988, abandoned, and Ser. No. 810,015, Dec. 17, 1985, abandoned.

[51] Int. Cl.⁵ ............................................. A61M 25/00
[52] U.S. Cl. ................................. 604/280; 128/207.14
[58] Field of Search ............... 128/658, 737, 656, 653, 128/303.1, 207.14–207.17, 200.26, 653 R, 653 SC; 604/53, 282, 280, 270, 100, 194

[56] References Cited

U.S. PATENT DOCUMENTS

| | | | |
|---|---|---|---|
| 2,765,792 | 10/1956 | Nichols | 128/200.26 |
| 2,786,469 | 3/1957 | Cohen | 128/200.26 |
| 3,618,613 | 11/1971 | Schulte | 604/282 |
| 3,847,197 | 6/1973 | Caillouette et al. | 128/656 |
| 3,854,229 | 12/1974 | Morgan | 40/594 X |
| 4,063,561 | 12/1977 | McKenna | 128/207.15 |
| 4,173,228 | 11/1979 | Van Steenwyk et al. | 128/653 R |
| 4,211,741 | 7/1980 | Ostoich | 604/280 |
| 4,244,362 | 1/1981 | Anderson | 128/200.26 |
| 4,265,276 | 5/1981 | Hatada et al. | 604/280 |
| 4,416,286 | 11/1983 | Iinuma et al. | 128/600.05 |
| 4,431,005 | 2/1984 | McCormick | 128/207.14 |
| 4,444,186 | 4/1984 | Wolvek et al. | 606/194 |
| 4,445,501 | 5/1984 | Bresler | 600/12 |
| 4,447,239 | 5/1984 | Kruetten | 604/282 |
| 4,571,240 | 2/1986 | Samson et al. | 604/96 |

FOREIGN PATENT DOCUMENTS

| | | | |
|---|---|---|---|
| 2404656 | 8/1975 | Fed. Rep. of Germany | 604/282 |
| 3239032 | 4/1984 | Fed. Rep. of Germany | 604/282 |
| 0940777 | 7/1982 | U.S.S.R. | 128/658 |

OTHER PUBLICATIONS

Surgitek ® Advertisement from Medical Engineering Corp., Aug. 16, 1976.

*Primary Examiner*—John D. Yasko
*Assistant Examiner*—Adam J. Cermak
*Attorney, Agent, or Firm*—Fish & Richardson

[57] ABSTRACT

A catheter and a method of making the same, which catheter has a means for interferring with an electromagnetic field to allow accurate detection of the catheter through tissue, the catheter comprising a first tube extruded over a continuous, solid core material having a diameter equivalent to the desired diameter of the inner passageway of the catheter, bands of metal fused to the first tube at various locations, and a second tube which is extruded over the first and the metal bands. The double-walled continuous tube is then cut into individual tubes and the core material is removed to form the catheter of this invention, which has a smooth outer surface and an embedded metal band.

7 Claims, 4 Drawing Sheets

DOUBLE WALL CATHETER WITH INTERNAL PRINTING AND EMBEDDED MARKER

This is a continuation of co-pending application Ser. No. 196,047 filed on May 19, 1988, now abandoned and Ser. No. 810,015 filed on Dec. 17, 1985, now abandoned.

FIELD OF THE INVENTION

This invention relates to a catheter with a metal element embedded within its wall at a preselected location in order to allow the catheter to be detected accurately inside a patient, and a method of making the same.

BACKGROUND OF THE INVENTION

Catheters are used in a variety of medical applications, and in some, they must be precisely positioned initially and kept in that position despite movement of the patient or other factors One example of such catheters are tracheal tubes. With many medical patients, it is necessary to insure that the breathing passageway is kept open at all times, and this is accomplished by a tracheal tube. The tube is inserted through the patient's mouth or nose, and it extends down into the patient's throat and into the patient's windpipe or trachea. Air can then pass through the tube lumen into and out of the patient's lungs. The principal drawback of these tubes is that there is not much room for error in placement of the distal or internal end of the tube inside the patient s windpipe in order for the tracheal tube to be effective, particularly with a pediatric patient. In fact, the distal end of the tube must be kept at a relatively specific position, which is at about the midpoint of the trachea below the vocal cords and above the carina. If the tube is inserted too far down into the trachea, its distal end may extend into the bronchial tree for one lung, and thus the other lung will receive an inadequate supply of air and may collapse. On the other hand, if the distal end of the tube is not inserted far enough into the trachea, it may interfere with the vocal cords, or it may be accidentally extubated and enter the esophagus with the result that air will not reach the lungs It is somewhat difficult to position a tracheal tube properly in the trachea, and in fact, tracheal tubes are usually inserted with the aid of a laryngoscope. Once properly in place, the tube is usually anchored by inflating a cuff on the distal end (for adult tracheal tubes) and taping the proximal or external end to the patient's skin. Nevertheless, even if properly positioned initially, and despite being secured in place, the tubes can and do move because of normal movement of the patient as well as during medical procedures such as surgery. Thus, the position of the distal end of the tube must be frequently monitored.

In the prior art, this monitoring is usually done by indirect means such as auscultation of the chest, which involves listening to breathing sounds for both lungs. It is also done by checking for chest motion, as well as generally observing the depth of insertion of the tube based on markings on the portion of the tube outside of the patient's mouth. These methods are generally unsatisfactory as they all really depend on a physiologic response of the patient as the basis for determining the position of the tube. The other common method for monitoring tube position is by X-ray. In addition to being expensive and exposing the patient to radiation, it also has the principal drawback that by the time the X-ray is taken, developed and returned, the tube may have moved again. Accordingly, the X-ray technique is unsuitable, particularly in critical care or emergency situations, when such tubes are commonly used.

As might be expected, the positioning and monitoring problems are particularly acute with infants or pediatric patients, who have such tubes inserted in most critical care situations and for up to three-fourths of all surgery involving general anesthesia. There is much less margin for placement error in infants or pediatric patients because the tracheas are much shorter. Also, the tracheal walls of infants and children are fragile and much more susceptible to mucosal wall irritation and rupture, which could be caused by any abrupt surface discontinuity on the tube. For this and other reasons, tracheal tubes for infants do not have inflatable cuffs to anchor the distal ends in place. Thus, they are more susceptible to movement. Consequently, proper tube placement and monitoring are much more difficult and critical with pediatric tracheal tubes.

A new method of and apparatus for accurately determining the positioning of a tracheal tube inside a trachea is disclosed in McCormick U.S. Pat. No. 4,431,005 and its related patents, Bresler U.S. Pat. No. 4,445,501, and Bresler U.S. Pat. No. 4,416,289, all of which are incorporated herein by reference. In these, the position of a tracheal tube inside the trachea is determined by a device which generates a narrow electromagnetic field and detects disturbances in that field caused by a piece of metal placed around the outside of the distal end of the tracheal tube. The metal disturbs the narrow field even through biological tissue. Accordingly, the position of the distal end can be determined when the device detects the resulting field disturbance. The tube for use with this device is shown in the patents. It has a piece of metal wrapped around and secured to the outside of a commonly used plastic tracheal tube. The metal is then covered by a plastic coating.

Unfortunately, these particular tubes are unsatisfactory, particularly for pediatric patients, for a number of reasons. First, even though it has a thin coating, the metal band can still irritate a child's trachea very easily because it protrudes significantly from the outer wall surface of the tube. Moreover, the metal band cannot be protected by an inflatable cuff. Such cuffs are unsuitable for use with the fragile wall of an infant's trachea, and they would also cause insertion problems due to the narrow space in which the tube must fit. Further, the pediatric tracheal tubes have narrow lumens and thin walls, making them both flexible and easily compressible. Thus, wrapping the metal band too tightly around the preformed tube, as might occur occasionally during manufacture, might lead to a compression of the wall and the critical air passageway in the tube. (The allowable tolerance for the inside diameter of such tubes is a mere ±0.003 inches.) On the other hand, failure to wrap the band tightly might result in serious consequences if the band should dislodge during use.

Finally, there is one additional drawback which applies to prior art catheters in general (not merely those with metal bands and the like). All tracheal tubes contain printed labeling on the outside surface of the tube. The labeling includes certain required medical nomenclature as well as depth of insertion markings. The latter is to allow medical personnel to check the depth of insertion of the tube by examining the depth markings on the exposed portion. Unfortunately, the ink used to print the markings may come off when it is rubbed in the presence of moisture or anesthetic gas. These conditions frequently exist when the tube is in use, and often the depth markings at the exposed end are erased or obscured as a result. When this occurs, the tube may have to be replaced. Further, while there are standards limiting the toxicity of the ink used, the ink is nonetheless toxic to some degree, and it would be preferable to prevent its contact with tissue.

SUMMARY OF THE INVENTION

We have discovered a double-walled catheter having a means for interfering with a electromagnetic field embedded between its walls, the catheter comprises a first tube to which the means for interfering is fused at a selected location and a second tube disposed over the first (and the means for interfering) to complete the double-walled catheter. In addition, depth markings may be printed along the length of the first tube prior to the attachment of the second tube so that in the finished catheter the markings are protected by the second tube and thus both isolated from any tissue and not susceptible to erasure. The method for making this catheter generally comprises extruding the first tube, fusing the means for interfering in place and extruding the second tube over the first and the means for interfering.

In the preferred embodiment, a tracheal tube is comprised of a first or inner plastic tube of uniform wall thickness and a second or outer plastic tube of approximately equal thickness. Both tubes are generally cylindrical in shape and are disposed concentrically, with the outside surface of the first tube contacting the inside surface of the second tube. The first tube has a thin metal band, which serves as the interfering means, attached around its outside. The two tubes are fused together along their entire length except for an indentation in the inside wall surface of the second tube, which indentation provides space to be occupied by the metal band. Depth markings and other indicia for the tracheal tube are printed on the outside of the first tube and protected by the second tube. The resulting tracheal tube has an internal passageway of uniform, precise diameter. The outer surface of the tracheal tube is continuous, smooth and has no surface discontinuities at any point along its entire length. At the same time, the printing and the metal band are in effect embedded in the double wall structure of the tracheal tube itself.

The tube of the preferred embodiment is made by first extruding a continuous solid core with an outer diameter equal to the required inner diameter for the desired tracheal tube. The core, which is usually several thousand feet long, is then fed into an extruder which evenly extrudes a first thin tube of plastic (polyvinylchloride in the preferred embodiment) around the core over its entire length. This first tube has a uniform thickness of about one half that of the finished catheter. As the core material has a higher melting temperature than the tube material, the core remains solid during this extrusion process. At selected intervals, thin bands of metal foil are then wrapped around the first tube, which is still in place on the continuous solid core. One end of a metal foil band is fused to the first tube by a high electrical current discharge of short duration. The band is then wrapped around the first tube until the free end overlaps the end already fused to the tube. The overlapped portions are fused together to secure the band to the first tube. While the first tube is still on the core, depth markings are printed along the length of the first tube. The first tube and the core are then subjected to another extrusion process whereby a second tube of plastic, having a thickness of about half that of the finished catheter, is added. The second tube fuses to the first during this process, forming a continuous double-walled tracheal tube. A radiopaque marker in the form of a line extending the length of the tube is coextruded as part of the second tube. This marker is a standard one for such tubes and is used to help identify the tube in an X-ray. The tube is then cut at the appropriate places, and the core is removed to form the completed double-walled tracheal tube.

DESCRIPTION OF THE PREFERRED EMBODIMENT

Drawings

I turn now to a description of the preferred embodiments, after first briefly describing the drawings.

FIG. 9A to 9E shows the sequence of steps for attaching the metal foil to the inner or first tube; FIG. 10 is a simplified drawing of the extruder for forming the outer or second tube of the invention.

DESCRIPTION

Figure 1:
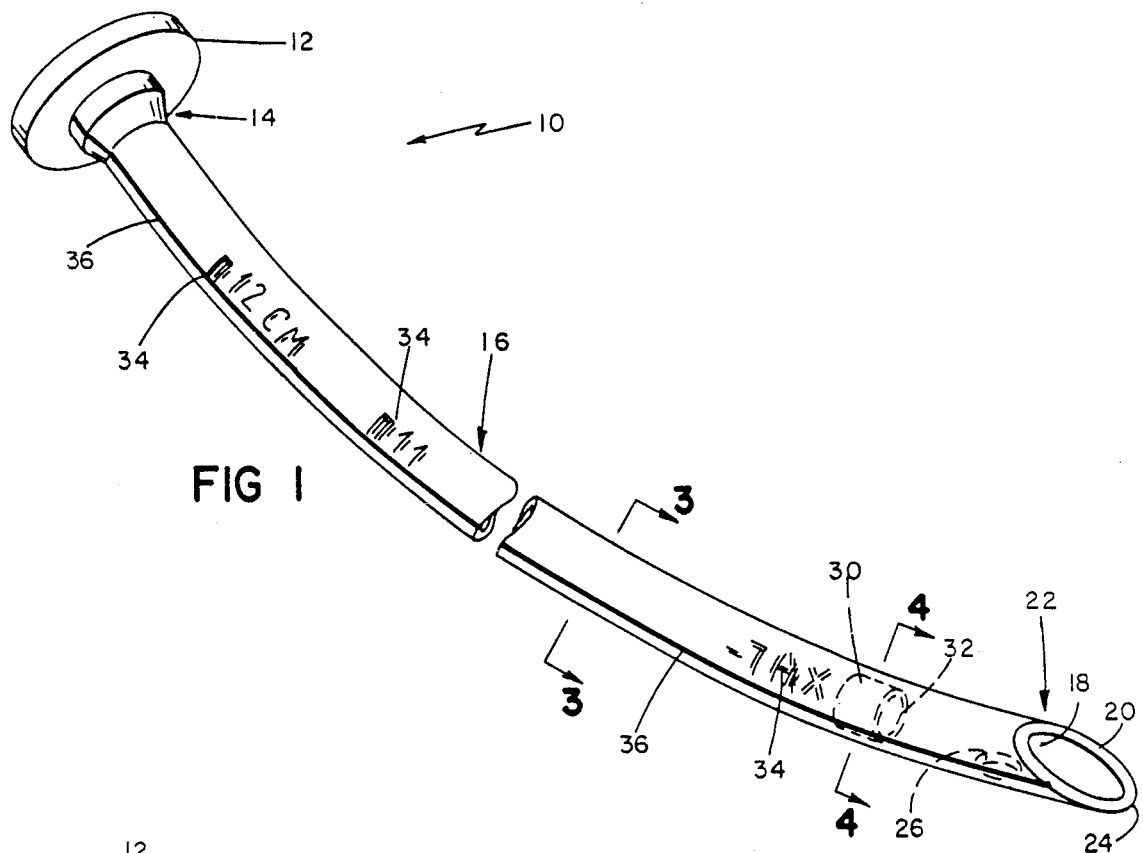
FIG. 1 is a perspective view of a double-walled tracheal tube of the invention.

Referring to FIG. 1, a double-walled catheter or tracheal tube according to the invention is shown at 10. The tube 10 generally has a connector endpiece 12 at the proximal end 14 of the tube 10 for attachment to a respiratory support system (not shown), and a plastic double-walled tubular section 16 surrounding a central air passageway 18. The tubular section 16 is connected to the endpiece 12, and the passageway 18 extends from the endpiece 12 to a beveled opening 20 located at a distal end 22 of the tube 10. The tip of the distal end 22 is identified as 24. A small hole 26, commonly known as a Murphy hole, is also located in the tubular section 16 at its distal end 22, and a cylindrical band of thin metal foil 30, having a distal edge 32, is encased within the tubular section 16 of the tube 10 near the distal end 22 and the hole 26. The distance along the length of the tube 10 between the distal edge 32 of the metal band 30 and the distal tip 24 is determined by the proposed medical use of the catheter tube and the desired anatomical location for the metal band 30. For tracheal tubes in general, proper medical use requires that the tip 24 be positioned at a suitable distance above the carina and below the vocal cords. In order to achieve this positioning, the metal band 30 should be at the anatomical tracheal location defined by the suprasternal notch. In order to assure this with proper tube positioning, the distance between the tip 24 and distal edge 32 of the metal band 30 will vary according to the internal diameter tube size appropriate to various patient sizes. The following table gives the approximate distances for pediatric tracheal tubes of this invention for each commonly used type according to internal diameter size.

| Tube Size (Internal Diameter) | Distance from tip 24 to the distal edge 32 of the metal band 30 |
| --- | --- |
| 2.5 mm | 1.0 cm |
| 3.0 mm | 1.3 cm |
| 3.5 mm | 1.5 cm |
| 4.0 mm | 2.0 cm |
| 4.5 mm | 2.5 cm |
| 5.0 mm | 3.0 cm |
| 5.5 mm | 3.3 cm |
| 6.0 mm | 3.6 cm |
| 7.0 mm | 4.0 cm |
| 8.0 mm | 4.5 cm |

Also encased within the double-walled tubular section 16 are the depth markings and indicia 34. A radiopaque line 36 is an integral part of the second or outer tube wall in one preferred embodiment. The line 36 extends the length of the tube 10 while the markings and indicia 34 extend between the metal band 30 and the endpiece 12.

Figure 2:
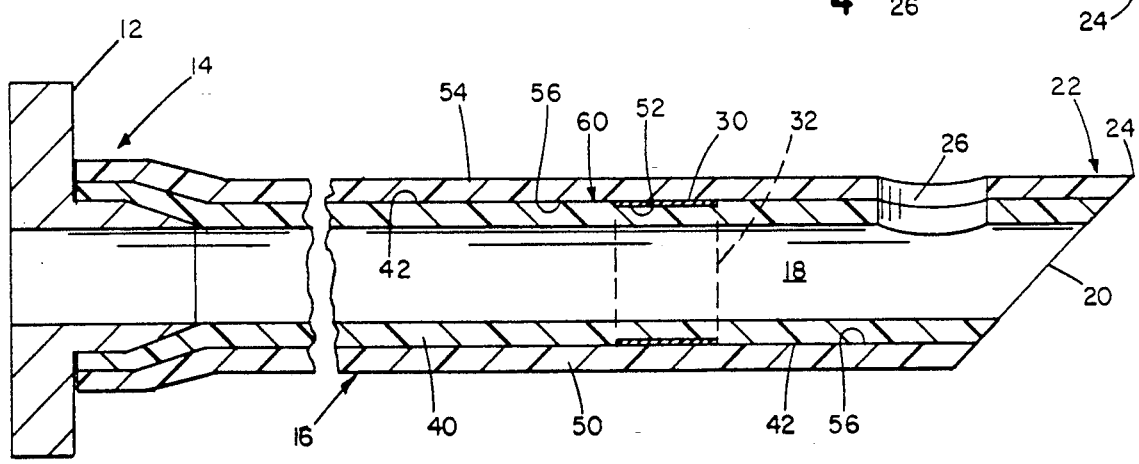
FIG. 2 is a lengthwise cross-sectional view of the double-walled tracheal tube of this invention.

Referring to FIG. 2, the tubular section 16 of the invention is comprised of an inner or first tube 40 and an outer or second tube 50. The first tube 40 has a uniform wall thickness along its length and an outside surface 42 on which the depth markings and indicia 34 are printed and the metal band 30 is disposed. The second tube 50 also has a uniform wall thickness along its entire length except at an indentation 52 which is occupied by the metal foil 30. The outer surface 54 of the second tube 50 is of uniform dimensions along its entire length resulting in a smooth, continuous outer surface for the double-walled tubular section 16. Because the second tube 50 provides this indentation 52 for the metal band 30 to occupy, the metal band does not introduce any surface discontinuities in the form of bumps or protrusions to the outer surface 54 of tubular section 16. This is important because outside wall smoothness is required in tracheal tubes, particularly in pediatric ones.

As shown in FIG. 2, there is a seam 60 between the first tube 40 and the second tube 50. The outside surface 42 of the first tube 40 contacts the inner surface 56 of the second tube 50. The two tubes 40, 50 are fused together at these contacting surfaces to form the cylindrical seam 60 that extends the entire length of the tubular section 16, except in the portion occupied by metal band 30. The seam 60, however, does include the areas of the depth markings and indicia 34. The seam 60 between the two tubes 40, 50 may be created by any number of well known thermoplastic processes and is ideally formed when outer tube 60 melts partially on top the outside surface 42 of inner tube 40. The specific method by which this is accomplished for the preferred embodiment will be discussed hereinafter. (In the preferred embodiment, the seam 60 is visible under slight magnification, particularly when the tube is cut cross-sectionally.)

Figure 3:
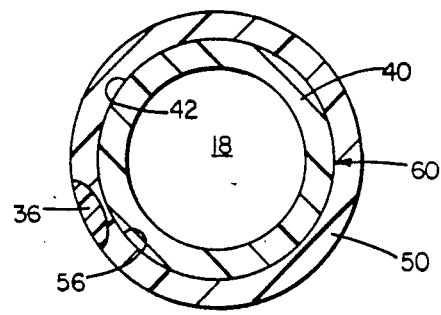
FIG. 3 is a cross-sectional view taken along lines 3—3 of FIG. 1.

Also shown in FIG. 3 is the cross section of radiopaque stripe 36 which runs the entire length of tubular section 16. The radiopaque stripe 36 may be included as an integral part of either or both tubes 40, 50 and can be formed by various well known coextrusion processes, the preferred one also to be discussed hereinafter.

Figure 4:
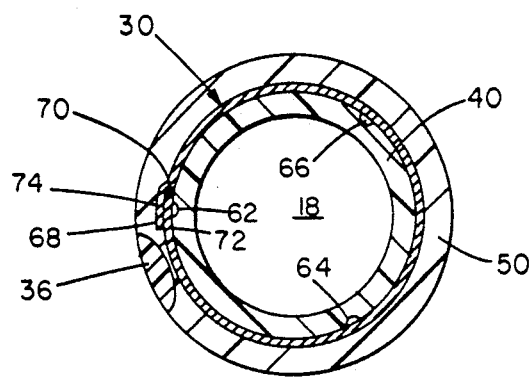
FIG. 4 is a cross-sectional view taken along lines 4—4 of FIG. 1.
Figure 5:
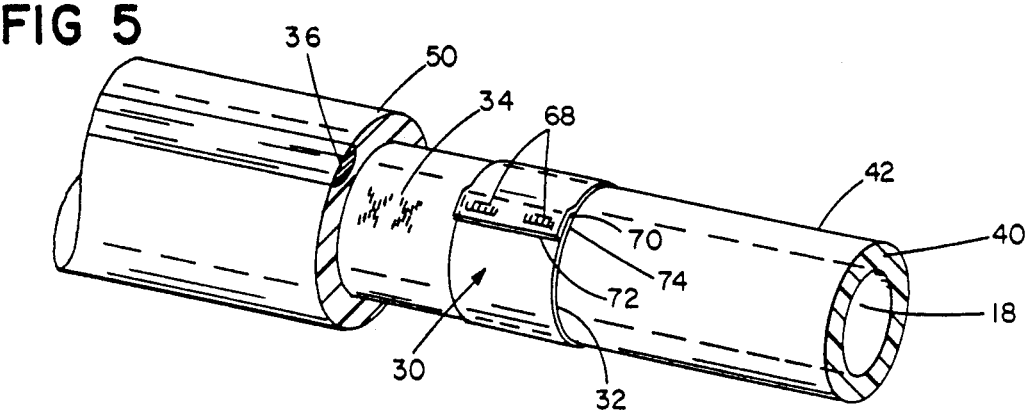
FIG. 5 is a perspective view of the end of the tracheal tube of this invention with a portion of the second or outer tube cut away.

As best shown in FIGS. 4 and 5, the metal band 30 is attached to the first tube 40 at three fusion sites 62, 64, 66 disposed at about 120° apart around the circumference of the tube 40. (In the preferred embodiment, only fusion site 62 is used. Sites 64 and 66 are optional.) First, the primary or leading edge 70 of the metal band 30 is welded to the first tube 40 at fusion site 62. The metal band is then wrapped around the tube 40 and welded to the tube 40 at fusion sites 64 and 66, as shown in FIG. 4. When fully wrapped around the tube 40, a trailing edge 72 of the metal band 30 overlaps the primary edge 70 of the band 30. This forms an overlap area 74. A welded overlap joint 68 is made at this overlap area 74, which effectively fuses the metal band 30 to itself. There are various means of attaching the metal band 30 to the tube 40. The preferred process for doing so in this invention is described later.

The tube 10 is made in the following manner. First, a continuous solid core 80 is made having an outer diameter which is identical to the inner diameter of the desired air passageway 18 for the tube 10. For example, in the case of a standard 2.5 mm (internal diameter) tracheal tube, the diameter of the core 80 would be 0.098 inches with a tolerance of ±0.003 inches. The core 80 itself may be made of any of a number of materials including metal wire. However, in the preferred embodiment, the core 40 is extruded of Celcon ®(M90-04) available from the Celanese Corporation. Celcono ® is a suitable core material because Celcon ® forms a rigid and smooth core which has a higher melting point than the usual materials used for the tube itself, thereby enabling the tube materials to be extruded over it without fusing to the core. The Celcon ® also has significant inherent lubricious properties enabling it to be easily pulled out of a tube extruded over it. (The metal wire also used for such a core does not slide as well and usually must be stretched to be removed.) Also, as the Celcon ® has no biological toxicity, there is no concern regarding any minute particles that might be left in the tube.

Figure 6:
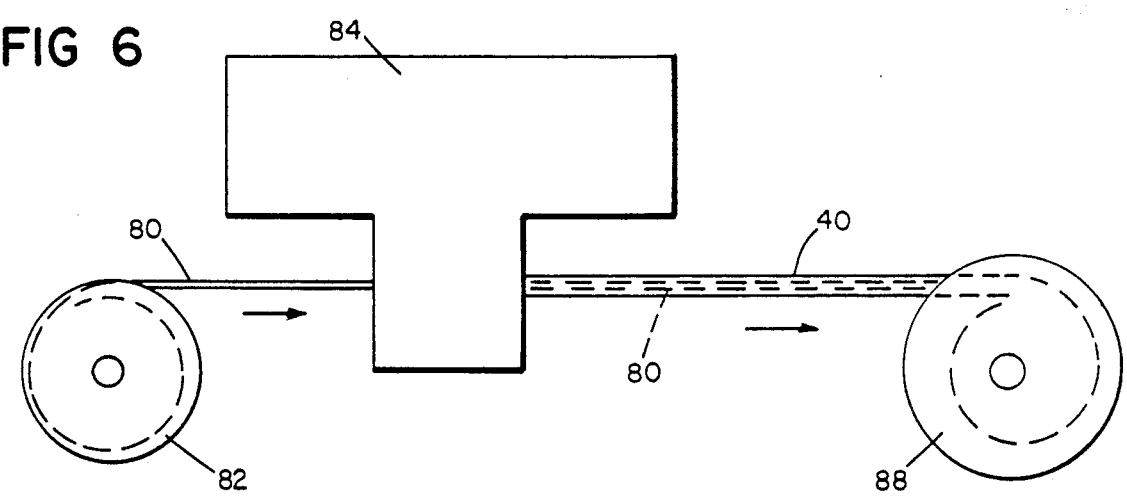
FIG. 6 is a simplified drawing of the extruder for making the inner or first tube.

The core 80 is then wrapped on a feed spool 82 and fed to the extruder 84 as shown in FIG. 6, which in the preferred embodiment extrudes a polyvinylchloride (PVC) layer over the core 80. This layer is actually the first tube 40. Preferably, the material used to extrude the first layer 40 is PVC 8511A-02 of Colorite Unichem, Inc. However, polyurethane, silicone-rubber or teflon could be used instead. In any case, because of the lower melting temperature of the tube material (the PVC in the preferred embodiment), the first tube 40 does not fuse to the core 80 during this process. Instead, the first tube 40 coats the entire core 80 to a uniform thickness over the entire length. In the case of a 2.5 mm tracheal tube, this thickness would be about 0.010 inches. Other wall thicknesses between 0.060 inches and 0.010 inches may be used, however. The core 80 with the first tube 40 is then drawn up on a take-up spool 88. At this point, the continuous core and the extruded first tube 40 may be several thousand feet long. The actual extruding process itself may be done on a variety of well-known pieces of equipment or by several companies which do such work including the Adam Spence Corp. of Wall, New Jersey, Berkley & Co. of Spirit Lake, Iowa, or Norton Health Care Products of Wayne, New Jersey.

Figure 7:
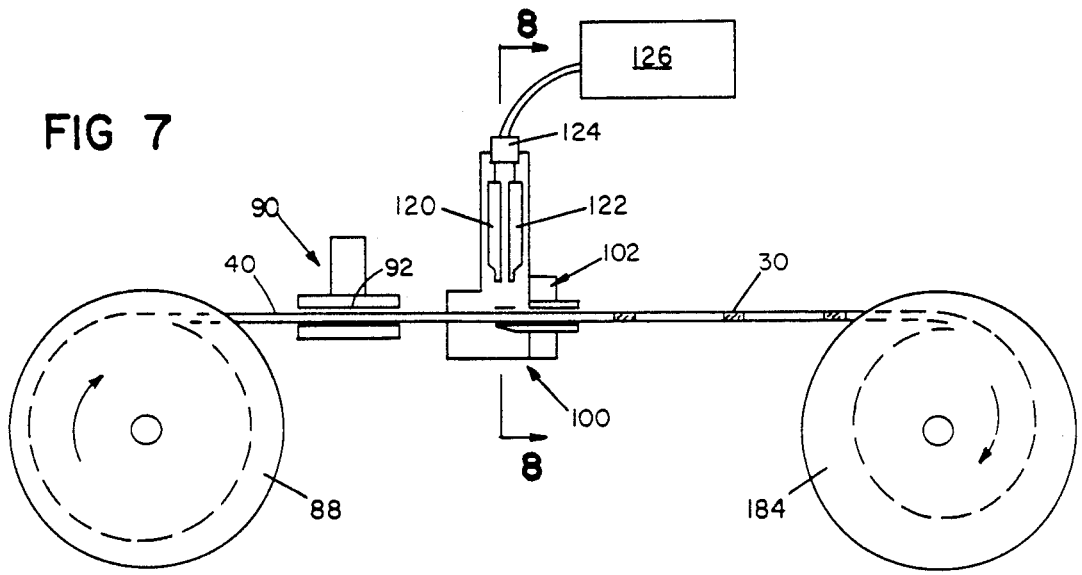
FIG. 7 is a simplified cross-sectional view of the printer unit and assembler unit for adding depth markings and for attaching the metal foil to the inner or first tube respectively.
Figure 8A:
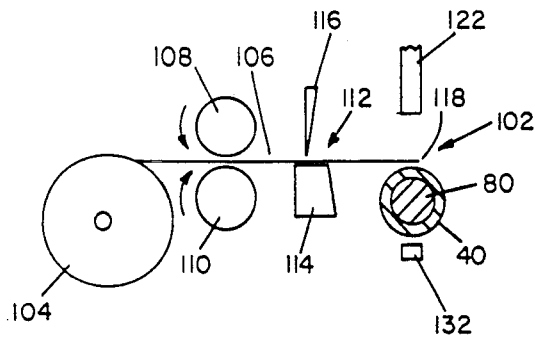
FIG. 8A and 8B are side views taken along lines 8—8 of FIG. 7 showing the manner in which the metal foil is fed to the assembler unit.

Referring to FIG. 7, the take-up spool 88 is then unwound, and the core 80 with the first tube 40 is fed into a printer unit 90. Initially, the core 80 with the first tube 40 moves into a print station 92 in the printer unit 90. At the print station 92, the depth markings and indicia 34 are applied to the outer surface 42 of the extruded first tube 40. The core 80 with the tube 40 is then fed into an assembler unit 100, which is mainly comprised in the preferred embodiment of a Unitek Corporation welder, model PMI, S/N 11024, X2/230, 86F. The core 80 and the first tube 40 go through a workstation 102 in the unit 100. As shown in FIG. 8 (a cross-sectional view of FIG. 7 taken along lines 8—8), a supply reel 104 is disposed near the workstation 102 at a right angle to the direction of feed for the core 80 and first tube 40. The supply reel 104 carries several hundred feet of a strip of metal foil 106. The foil 106 is approximately 0.10 inches wide and 0.001 inches thick. The foil 106 is molypermalloy from the Arnold Engineering Corporation. The foil 106 is fed between advance wheels 108, 110 and through a cutting station 112. The cutting station 112 is comprised of a block 114 and a cutting tool 116. The foil 106 passes over the block 114 below the cutting tool 116 so the leading edge 118 of the foil 106 is positioned tangentially to (and in contact with) the first tube 40 in the workstation 102. This positioning is just downstream (away from the spool 88) of the depth markings and indicia 34 just added by the printer unit 90.

Figure 8B:
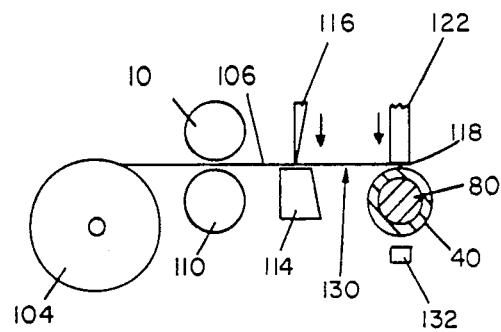
Figure 9A:
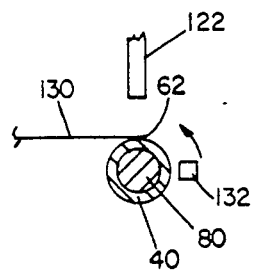
Figure 9B:
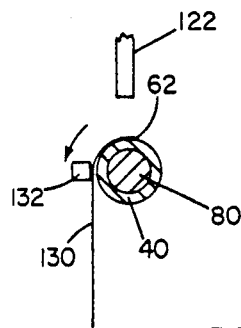
Figure 9C:
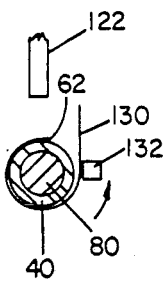
Figure 9D:
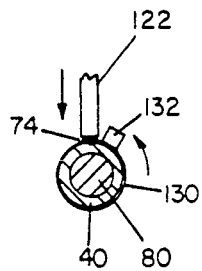

As shown in FIG. 7, a pair of welding heads 120, 122 are positioned above the leading edge 118 of the metal foil 106 and the first tube 40 in the workstation 102. When the leading edge 118 of the foil is in place, a controller 124 moves the welding heads 120, 122 down to contact the leading foil edge 118 and the first tube 40, as shown in FIG. 8B (for welding head 122). Actually, the heads 120, 122 press the leading edge 118 of the foil 106 against the first tube 40 at a pressure of 0.20 pounds, and the welding heads 120, 122 then briefly discharge an intense current. (The current is actually generated by a transformer 126 connected to the heads 120, 122). The current is 500 amps, and it is applied for 0.005 seconds. The welding current causes the foil 106 and the area of the first tube 40 immediately thereunder to fuse together forming weld 62 (as shown in FIG. 4). The short duration of the current, however, confines the melting to the immediate area of the foil and tube and to a depth of only a few thousandths of an inch into the tube 40. Thus, while welding at this pressure and current for this period of time does attach the foil to the tube, it does not affect the inner portion of the PVC tube or the core, even with the thinnest PVC wall.

Following the attachment of the leading edge 118 the cutting tool 116 falls, as shown in FIG. 8B, and it cuts the foil 106 so that only a short foil strip 130 is actually attached to the tube 40 by the weld 62. The strip 130 has a length just exceeding the outside circumference of the first tube 40.

As shown in FIG. 9, a rotating wrapping fixture 132 then moves around the first tube 40 and the core 80 in the direction shown by the arrow. This wraps the foil strip 130 around the first tube 40, as shown sequentially in FIGS. 9B, 9C, and 9D. As has been previously explained, the foil strip 130 is longer than the circumference of the first tube 40, and there is an area of overlap 74 when the foil strip 130 is wrapped around the tube 40, as shown in FIG. 4 and 9D. Once this overlap 74 is created, the welding heads 120, 122 are then brought down into contact with it (only head 122 is shown in FIG. 9), and the overlap 74 is fused to the portion of the foil strip 130 and tube 40 underneath it in the same manner the leading edge 118 of the foil was originally fused to the tube 40. The foil strip 130 has now become the metal band 30 surrounding the first tube 40. Alternately, other welding heads may be added to provide additional fusion joints at points intermediate between the leading edge 118 and the overlap 74. Such optional fusion joints are 64 and 66 shown in FIG. 4.

Once the metal band 30 is attached, that portion of the first tube 40 and the core 80 are then moved out of the workstation 102, and the process of attaching a metal band is repeated on another section of the first tube 40. This process continues until metal bands are attached at intervals along the entire continuous length of the core 80 and first tube 40. The distance between the metal bands is, of course, somewhat greater than the overall length of an individual tracheal tube.

Figure 10:
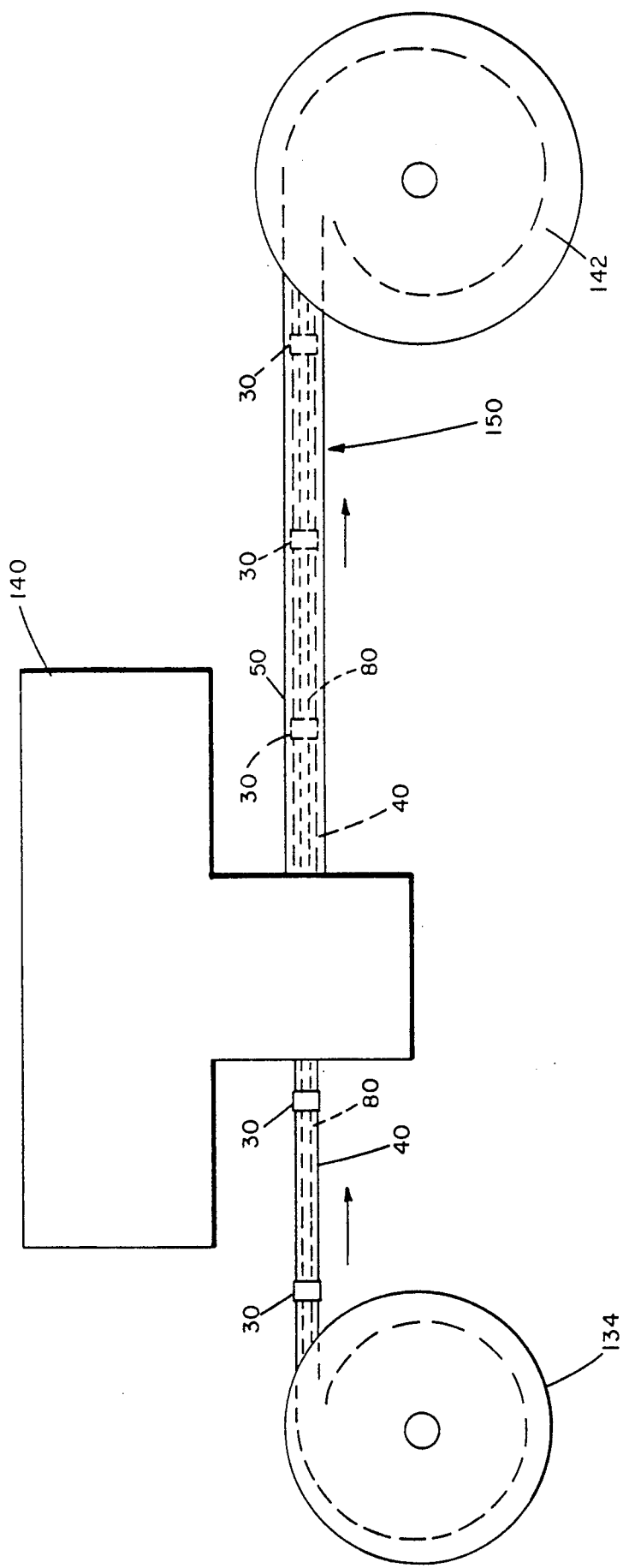
FIG. 10 is a simplified drawing of the extruder for forming the outer or second tube of the tracheal tube of this invention.

Finally, the banded and printed first tube 40 and core 80 are fed from the workstation 102 to a take-up spool 134, as shown in FIG. 7. The take up spool 134, with the banded and imprinted tube 40 and core 80, are then fed to another extruder 140 which extrudes a second tube 50 around it, as shown in FIG. 10. The resulting double-walled tube 150 is collected on spool 142. In this extrusion process, the first tube 40 fuses to the second outer tube 50, except where the metal bands 30 are located. The fusion of the two tubes 40, 50 forms the seam 60 resulting in the doubled-walled structure of the tracheal tube 10, the overall wall thickness of which is the same as that of conventional tracheal tubes. Accordingly, the second tube 50 is about half the thickness of the desired wall thickness of the tracheal tube. This extrusion process also forms the indentation 52 in the second tube 50 into which the metal band fits (see FIG. 2). Also, as part of the second extrusion process (using a crosshead extrusion method), the radiopaque line 36 is coextruded along the length of the second tube 50. The line 36 may be a barium, a bismuth or a tungsten base of the type usually used for such markers. The line 36 makes it easier to detect the tube in an X-ray, and is shown in FIG. 3 in cross-section. (The line 36, however, could be coextruded as part of the first tube 40.)

The outer diameter of the second tube 50 (and thus the outer diameter of the tubular section 16) is determined by the die fixture of the extruder 140 in the conventional manner. As a result, the outer surface of the second tube 50 is smooth and has no discontinuities, despite the presence of the metal band 30.

The resulting continuous double-walled tube 150 is next cut into segments, each slightly longer than a finished catheter. The cuts are made near the metal bands 30 so that when the tube is finished, the metal bands will be near the distal end 22. The preferred distances between tip 24 of the distal end 22 and the distal edge 32 of the metal band 30 have been previously disclosed herein.

The resulting tubes are then completed by removing the core 80, and finishing the tube. The core 80 is removed by cutting a small piece of tubing away from the core at one end. The then-protruding core 80 can then be easily pulled out. Once this is done, the tube is finished by cutting the tip at an angle 20, creating the Murphy hole 26, and adding the endpiece 12. The finished tube is smooth both inside and out with very precise internal and external diameter. In particular, the tube has smooth internal and external surfaces with no surface bumps, protrusions or discontinuities, and the metal band is secured within the tube, totally isolated from the tissue into which the tube is inserted. At the same time, the depth markings are also protected from erasure and contact with tissue.

Operation

In operation, the tube 10 is inserted into a patient so that the distal end 22 is disposed in the trachea. The proximal end 14 with its endpiece 12 extends out of the patient's mouth. The location of the distal end is then detected by the general method and apparatus disclosed in the patents mentioned earlier and incorporated herein by reference, which depend upon the metal band 30 disturbing a narrow electromagnetic field. Thus, the band can be easily and quickly located in the trachea in real time, and the tube repositioned, if necessary.

Other Embodiments

The metal band 30 may be attached to the first tube 40 by means other than electric welding. For example, laser welding systems may be used, such as from Laser Industries, Ind. of Lawrence, Massachusetts. Also various bonding agents may be used as well. For example, the foil may be bonded to the first tube 40 with a variety of cyanoacrylate rapid bonding agents from Loctite Corporation or Permabond Corporation. Other such bonding agents also exist.

Also, it is not necessary that the foil strip overlap itself as it is fitted around the first tube. Instead, its length could be less. Various types of metal powders may be used instead of the foil. These include various ferrites and METGLAS ® from the Allied Signal Corporation, which could be applied as paint metal pigment formulations in the same manner used to print the depth markings and indicia.

As the term is used therein, catheter is a general term and means a catheter of any type, including the tracheal tube of the preferred embodiment. It is understood, however, that the structure and method disclosed herein apply to catheters in general and not just tracheal tubes, which is merely one embodiment of the invention.

Other variations will occur to those skilled in the art. What I claim is:

1. A catheter for insertion into biological tissue to provide an opening therein, and when so inserted, only the distal end of said catheter being detectable outside the biological tissue by means of a narrow electromagnetic field, said catheter comprising:
   a double-walled tubular section having a proximal end and a distal end,
      said double-walled tubular section, which does not interfere with an electromagnetic field, comprising a first tube, said first tube extending the entire length of said catheter from the proximal end to the distal end, said first tube defining an internal passageway which also extends the length of said catheter, and having an outer-surface which extends the length of said catheter, and a second tube, said second tube extending the length of said catheter and being connected to the outer surface of said first tube over its entire length forming a seam therebetween, said second tube having a smooth outer surface which defines the outer surface of said double-walled tubular section, and
   a means for interfering with an electromagnetic field, said means for interfering being a small and narrow metal band attached to the outer surface of said first tube only at the distal end of said catheter, said metal band having a leading edge and a trailing edge which overlap when said band is wrapped around said first tube and which band is fused at least in part to said first tube, said means for interfering fitting into an indentation in an inner wall of said second tube at the distal end so as to maintain the smooth outer surface of said second tube without any protrusion at the means for interfering, said means for interfering disturbing a narrow electromagnetic field directed towards it even through biological tissue, but said means for interfering being so small and narrow a metal band so as to only disturb the field when the field is proximate to said means for interfering.

2. The cathetor of claim 1 wherein said first tube and said second tube are fused together along their respective lengths, except at said means for interfering, forming said seam therebetween.

3. The catheter of claim 1 wherein said second tube is transparent and said outer surface of said first tube has depth marking printed thereon.

4. The catheter of claim 1 wherein said said indentation fits over said metal band.

5. The catheter of claim 4 wherein said metal band is fused to said first tube.

6. The catheter of claim 1 wherein a radiopague stripe is included along the length of either said first tube or said second tube.

7. A catheter for insertion into biological tissue to provide an opening therein, and when so inserted, only the distal end of said catheter being detectable outside the biological tissue by means of a narrow electromagnetic filed, said catheter comprising:
   a double-walled tubular section having a proximal end and a distal end,
      said double-walled tubular section, which does not interfere with an electromagnetic field, comprising a first tube, said first tube extending the entire length of said catheter from the proximal end to the distal end, said first tube defining an internal passageway which also extends the length of said catheter, and having an outer surface which extends the length of said catheter, and a second tube, said second tube extending the length of said catheter and being connected to the outer surface of said first tube over its entire length forming a seam therebetween, said second tube having a smooth outer surface which defines the outer surface of said double-walled tubular section, and
   a means for interfering with an electromagnetic field, said means for interfering being a small and narrow metal band attached to the outer surface of said first tube only at the distal end of said catheter, said metal band having a leading edge and a trailing edge, which said band is partially wrapped around said first tube with said edges fused to said tube, said means for interfering fitting into an indentation in an inner wall of said second tube at the distal end so as to maintain the smooth outer surface of said second tube without any protrusion at the means for interfering, said means for interfering disturbing a narrow electromagnetic field directed towards it even through biological tissue, but said means for interfering being so small and narrow a metal band so as to only disturb the field when the field is proximate to said means for interfering.

* * * * *